United States Patent
Imai

(10) Patent No.: US 8,720,434 B2
(45) Date of Patent: May 13, 2014

(54) MEDICINE EJECTION DEVICE AND CONTROLLING METHOD THEREOF

(75) Inventor: Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 949 days.

(21) Appl. No.: 12/675,337

(22) PCT Filed: Nov. 4, 2008

(86) PCT No.: PCT/JP2008/070368
§ 371 (c)(1),
(2), (4) Date: Feb. 25, 2010

(87) PCT Pub. No.: WO2009/063814
PCT Pub. Date: May 22, 2009

(65) Prior Publication Data
US 2010/0206307 A1   Aug. 19, 2010

(30) Foreign Application Priority Data
Nov. 16, 2007   (JP) .................................. 2007-298173

(51) Int. Cl.
*A61M 11/00* (2006.01)

(52) U.S. Cl.
USPC .................................. 128/200.14; 128/200.22

(58) Field of Classification Search
USPC ............. 128/200.14–200.19, 200.21–200.23; 604/141, 143, 154, 155
See application file for complete search history.

(56) References Cited

U.S. PATENT DOCUMENTS

| | | | |
|---|---|---|---|
| 7,513,253 B2 | 4/2009 | Kobayashi et al. | 128/203.21 |
| 7,856,975 B2 | 12/2010 | Nobutani et al. | 128/200.14 |
| 2006/0184124 A1 * | 8/2006 | Cowan et al. | 604/155 |
| 2007/0062520 A1 | 3/2007 | Nobutani et al. | 128/200.14 |
| 2007/0227534 A1 | 10/2007 | Nobutani et al. | 128/200.14 |
| 2009/0188494 A1 | 7/2009 | Imai et al. | 128/203.12 |

FOREIGN PATENT DOCUMENTS

| | | | |
|---|---|---|---|
| EP | 00/25844 | 5/2000 | |
| JP | 05-201018 | 8/1993 | |
| JP | H05-201018 | 8/1993 | ............... B41J 2/175 |

(Continued)

OTHER PUBLICATIONS

Office Action issued Jul. 10, 2012, in counterpart Japanese Patent Application No. 2007-298173, and translation.

(Continued)

*Primary Examiner* — Nathan R Price
(74) *Attorney, Agent, or Firm* — Fitzpatrick, Cella, Harper & Scinto

(57) ABSTRACT

The invention provides a medicine ejection device which provides stable ejection even when a reservoir with high sealability is used and can eject an appropriate amount of medicine. A medicine ejection portion 1 includes an ejection nozzle 1a for ejecting a medicine and an element 1b which generates energy for ejecting the medicine from the ejection nozzle 1a, and is connected to a medicine storing portion 2 for storing the medicine. The medicine storing portion 2 is blocked from the outside air except a path through the ejection nozzle 1a, so that when the medicine is ejected from the ejection nozzle 1a, a pressure difference is formed between the outside and the inside of the medicine storing portion 2. A pressure unit 3 which is a feature of the present invention pressurizes a movable wall 5 when ejecting a medicine, which is displaced so that the volumetric capacity of the medicine storing portion 2 decreases due to the pressure difference.

7 Claims, 13 Drawing Sheets

(56) References Cited

FOREIGN PATENT DOCUMENTS

| | | | | |
|---|---|---|---|---|
| JP | 2002-528676 | 9/2002 | ............ | F04B 13/00 |
| JP | 2004-283245 | 10/2004 | ............ | B24B 49/10 |
| JP | 2004-290593 | 10/2004 | ............ | A61M 11/00 |
| JP | 2007-075259 | 3/2007 | ............ | A61M 15/00 |
| JP | 2007-077848 | 3/2007 | ............ | F04B 13/00 |

OTHER PUBLICATIONS

Office Action dated Dec. 7, 2011, issued by Chinese (P.R.C.) patent office in counterpart Chinese application 200880115600.8, with translation.

* cited by examiner

MEDICINE EJECTION DEVICE AND CONTROLLING METHOD THEREOF

TECHNICAL FIELD

This invention relates to a medicine ejection device which is configured to allow a user to carry and use, and can be used in an inhaler for making a user inhale a medicine, and to a controlling method thereof.

BACKGROUND ART

An inhaler is developed which ejects micro-droplets of a medicine into an air flow path through which inhaled air via a mouthpiece flows by using an ejection principle in an ink jet system, and makes a user inhale (cf. Japanese Patent Application Laid-Open No. 2004-290593 and Japanese Patent Application Laid-Open No. 2004-283245). This type of an inhaler has an advantage of being capable of precisely spraying a specified amount of a medicine with a uniformized particle size.

A basic configuration of such a medicine ejection device includes an ejection head in which an ejection energy generating element such as an exothermic element is arranged, and a reservoir for storing the medicine to be supplied to the ejection head therein. When the reservoir is a simple closed container, as the medicine is ejected and the amount of the medicine in the reservoir decreases, a negative pressure is generated in the reservoir and the ejection performance decreases. For this reason, it has been necessary to take such countermeasures as the followings for the reservoir.

The countermeasure firstly includes a method of employing a structure in which a reservoir communicates with the atmosphere right before ejection starts. The structure is adopted in an ink jet printer which is a known art. However, when the reservoir stores a medicine in an amount of being inhaled multiple times, it is impossible to employ the structure of making the reservoir communicate with the atmosphere, because of needing to prevent a medicine remaining in the reservoir after the apparatus has been used once from changing its concentration and being denatured, so that the reservoir is required to have high gas barrier properties and sealability. The circumstance is the same also in the case when it is unfavorable for a medicine to contact air.

In the case, the reservoir may be a flexible container that has such a structure as to be crashed along with ejection (Japanese Patent Application Laid-Open No. 2004-290593). For instance, the reservoir can be made from a polyester film on which aluminum has been deposited. Alternatively, when a main body of the reservoir is a glass container or the like, it is necessary to make the reservoir into such a structure in which the one end of the container is blocked with a rubber plug, and the volumetric capacity of the reservoir decreases along with ejection.

In the case when the reservoir having such high sealability is used, a pressure difference between the outside and the inside of the reservoir increases as a medicine continues being ejected. Even when the negative pressure in the reservoir increases in this way, a considerable power is required to deform the flexible reservoir with a force caused by the negative pressure, or reduce the volumetric capacity by sliding the rubber plug with respect to the glass container. The above description will be made in the case of the glass container. When a force applied to the plug due to the negative pressure in the reservoir has exceeded the greatest static frictional force between the glass container and the plug, the plug starts moving. If the plug is more tightly adapted against the glass container in order to keep high sealability, the plug does not move until the negative pressure reaches a corresponding high value.

On the other hand, it is elucidated that as the negative pressure in the reservoir increases, a performance of the ejection from an ejection head decreases. When a medicine is ejected from a head with a nozzle diameter of 3 μm, an ejection amount does not decrease until the internal pressure of the reservoir reaches the vicinity of −5 kPa, but when having the internal pressure exceeds −5 kPa, the ejection amount decreases little by little, and when the internal pressure reached −20 kPa, the inhaler drew air through the ejection head and could not eject the medicine any more. For this reason, in order to realize a stable ejection, it is possible to keep the negative pressure in the reservoir to a predetermined value or lower (in the above described case, −5 kPa) as accurately as possible during the ejection period of time.

Because of this, an inhaler with the use of a conventional reservoir having high sealability decreases its ejection performance as the inhaler continues ejection, and sometimes could not eject a medicine though depending on a case.

DISCLOSURE OF THE INVENTION

An object of the present invention is to provide a medicine ejection device which provides stable ejection even when a reservoir with high sealability is used and can eject an appropriate amount of medicine.

There is so-called an insulin pump and the like as a medicine-administrating device having a structure of plugging a container made from glass or the like, which is described in Japanese Patent Application Laid-Open No. 2002-528676. However, the insulin pump is different from an ink jet type of a medicine ejection device and has not an ejection energy generation element in an ejection nozzle, so that there is no room for the insulin pump to cause the problem of the present invention. The insulin pump extrudes a medicine by using a micro-feeding mechanism which pushes a plug.

With respect to such problems, a medicine ejection device for ejecting a medicine according to the present invention, which includes a medicine ejection portion having an ejection nozzle and an element that generates energy for ejecting a medicine from the ejection nozzle, and a medicine storing portion that is connected with the medicine ejection portion and stores the medicine therein, characterized in that the medicine storing portion is blocked from the outside air except a path through the ejection nozzle, includes a movable wall which is displaced so that the volumetric capacity of the medicine storing portion can be decreased by a pressure difference between the inside and the outside of the medicine storing portion, which is caused by the ejection of the medicine through the ejection nozzle, and includes a pressure unit for pressurizing the movable wall so as to decrease the pressure difference.

In addition, a method for controlling the medicine ejection device for ejecting a medicine according to the present invention which includes a medicine ejection portion having an ejection nozzle and an element that generates energy for ejecting a medicine from the ejection nozzle, and a medicine storing portion that is connected with the medicine ejection portion, is blocked from the outside air except a path through the ejection nozzle and stores the medicine therein, characterized in that the method includes the steps of:

starting the pressurization of a movable wall which is displaced so that the volumetric capacity of the medicine storing portion can be decreased, by a pressure difference between the inside and the outside of the medicine storing portion, which is caused by the ejection of the medicine through the ejection nozzle; and driving the element in a state of pressurizing the movable wall to make the element eject the medicine.

The medicine ejection device according to the present invention can decrease a volumetric capacity of a reservoir at a stage in which a negative pressure generated in the reservoir is lower than that in a conventional device, and accordingly can realize stable ejection.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Figure 1:
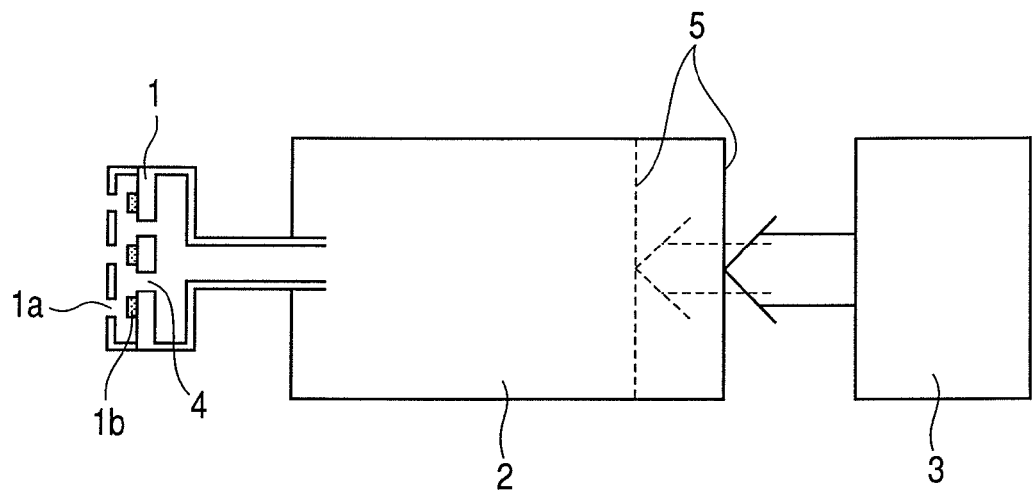
FIG. 1 is a view illustrating a conceptual structure of a medicine ejection device according to the present invention.

Preferred embodiments of the present invention will now be described in detail in accordance with the accompanying drawings.

However, the same component will be affixed by the same reference numeral as a general rule, and the description will be omitted.

FIG. 1 is a view illustrating a conceptual structure of a medicine ejection device according to the present invention. A medicine ejection portion 1 includes an ejection nozzle (nozzle) $1a$ for ejecting a medicine and an element $1b$ which generates energy for ejecting the medicine from the ejection nozzle $1a$. The element $1b$ for generating the ejection energy imparts the ejection energy to the medicine which has come through a medicine supply port 4. Thereby, a medicine is ejected from the ejection nozzle $1a$.

A medicine storing portion 2 for storing the medicine to be ejected is connected with the medicine ejection portion 1, and is blocked from the outside air except a path through the ejection nozzle $1a$. Accordingly, when a medicine is ejected from the ejection nozzle $1a$, and the amount of the medicine stored in the medicine storing portion 2 decreases, a pressure difference results in being formed between the inside and the outside of the medicine storing portion 2. The medicine storing portion 2 has a movable wall 5 therein, and is displaced so that the volumetric capacity of the medicine storing portion 2 decreases due to the pressure difference.

Here, the medicine ejection portion (ejection head) 1 has an arbitrary element for generating ejection energy. A thermoelectric transducer for applying thermal energy to a medicine or an electromechanical transducer for applying mechanical energy to the medicine can be illustrated. In other words, a method for ejecting the medicine can illustrate a method of imparting thermal energy to a medicine through the thermoelectric transducer and making the thermoelectric transducer eject the medicine (thermal jet type), and a method of ejecting the medicine by using a vibratory pressure of an electromechanical transducer (for instance, piezoelectric element) which imparts mechanical energy to the medicine (piezo-jet type). The ejection method can be selected according to a type of the medicine and the like.

When a thermal jet type has been employed, it is possible to enhance an aperture size of an ejection nozzle, the heat quantity of a thermal pulse to be used for an ejection, the size accuracy of a micro-heater as a thermoelectric transducer and reproducibility, with regard to an individual ejection head. Accordingly, the thermal jet type can achieve a narrow distribution of droplet sizes. The thermal jet type also has a low manufacturing cost for the head and can be sufficiently applied to a small device which needs to replace the head frequently. Accordingly, when portability and convenience are required to the medicine ejection device, it is possible to adopt an ejection principle of the thermal jet type in particular.

The outline of a medicine storing portion (reservoir) 2 will now be described, though the specific structure will be described later with reference to exemplary embodiments. The reservoir can employ a structure in which a glass container having both ends opened is employed as a main body and one end of them is blocked with a member such as a rubber plug. The other end is connected to an ejection head 1. The volumetric capacity of the reservoir is decreased when the plug slides and moves towards the inside of the glass container due to the above described pressure difference.

Alternatively, the reservoir may be a flexible container.

(Pressure Unit)

Figure 2A:
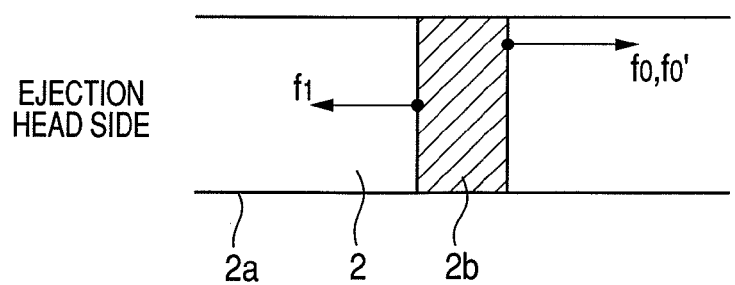
FIG. 2A and FIG. 2B are sectional views on a container and a plug schematically illustrating a force applied to a plug $2b$ in the case (2B) of using a pressure unit of a medicine ejection device according to the present invention, and in the case (2A) of not using the pressure unit.
Figure 2B:
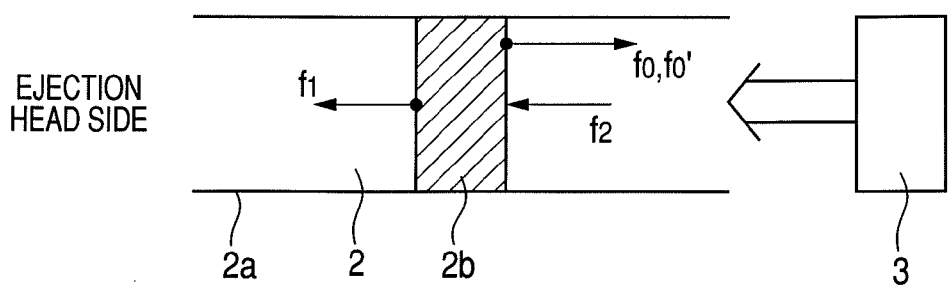

A pressure unit 3 which is a feature of the present invention pressurizes a movable wall 5 when ejecting a medicine. The pressure unit 3 will now be described with reference to the case where a medicine storing portion 2 includes a glass container 2a and a plug 2b of a movable wall. Specifically, the pressure unit 3 pressurizes the plug 2b with a predetermined pressure. FIG. 2A and FIG. 2B are sectional views of the container and the plug, which schematically illustrate the force to be applied to the plug 2b in the case (2B) of having used a pressure unit of a medicine ejection device according to the present invention and in the case (2A) of not using the pressure unit. Suppose that f0 is defined as the maximum static friction force working between the container 2a and the plug 2b, f0' as a kinetic frictional force working between the container 2a and the plug 2b, and f1 as a force applied to the plug 2b by a negative pressure which has been generated in the container 2a as a result of the medicine having been ejected. When the medicine ejection device does not have a pressure unit 3 (2A), the plug does not move immediately after the ejection has been started, and starts moving towards the inside of the container when f1 has exceeded f0. When the plug moves, f1 decreases and the plug continues moving till f1 balances with the kinetic frictional force f0'. When the medicine ejection device continues ejecting the medicine thereafter as well, the plug continues moving in a state in which f1 balances with f0'. When the plug stops moving after the ejection has been completed, a negative pressure corresponding to a force equal to f0' remains accumulated in the inside of the container.

On the other hand, suppose that the pressure unit 3 has continued applying the force of f2 to the plug during the whole period between the time just before the ejection is started and the time when the ejection is completed. In this case, the plug starts moving when f1 exceeds (f0-f2), and moves in a state in which f1 balances with (f0'-f2). Furthermore, only a negative pressure corresponding to a force equal to (f0'-f2) is accumulated in the inside of the container after the ejection has been completed.

Thus, by applying a fixed force f2 previously with the use of the pressure unit 3, the negative pressure applied to the inside of the container can be reduced throughout the period between the time when the ejection is started and the time when the ejection is completed.

In other words, when the pressure difference between the outside and the inside of the medicine storing portion exceeds a predetermined value, which results from the ejection of the medicine through the ejection nozzle, the volumetric capacity of the medicine storing portion decreases, but if the pressure unit 3 would pressurize the medicine storing portion, the predetermined value can be decreased.

The medicine used in the present invention has a concept of including not only a medicine of the medicinal compound which shows pharmacologic and physiologic actions, but also a component of scenting or flavoring, dye and pigment, in addition to the medicinal compound. The medicine may also include an arbitrary additive.

(Force to be Applied by Pressure Unit)

In theory, if a force equal to a kinetic frictional force f0' would be applied to a plug, the plug would continue moving in a state in which the internal pressure of a reservoir is 0 (zero), after the plug has started moving. However, when a medicine is ejected according to the principle of an ink jet system, the reservoir had better have some degree of a negative pressure therein. Specifically, the negative pressure is about −0.5 kPa to −4.5 kPa. Accordingly, the pressurizing force may be controlled so as to be capable of stably ejecting the medicine with the negative pressure of this level.

In addition, the force to be applied to the plug by the pressure unit 3 can be not higher than a kinetic frictional force f2. This is because when a force larger than f2 is applied to the plug, the force eventually pushes the plug too much after the plug has started moving, and may make the medicine leak from the ejection nozzle.

A value of a pressure to be applied to the plug 2b by the pressure unit is not always necessary to be constant during the ejection period. The pressure unit may just pressurize the plug so that the negative pressure in the reservoir can be kept at about −0.5 kPa to −4.5 kPa. In order to do this, it is possible to provide a sensor for measuring a pressure applied to the plug 2b by the pressure unit 3, and control the pressure unit according to a value measured by the sensor. As for a relationship between the value measured by the sensor and the control for the pressure unit, it is considered to control a pressurizing force into a predetermined range so that a negative pressure in the reservoir is kept at a predetermined range all through the ejection period as described above, for instance. Alternatively, the pressure unit may be controlled so as to always apply a constant pressure to the plug 2b based on the value of the sensor.

When it is desired to make a moving speed of the plug 2b constant during the ejection period, it is necessary to always apply a constant pressure to the plug 2b.

The pressure unit according to the present invention may pressurize a movable wall right before a medicine is ejected, and needs not to be operated when the device is not used (in preserved period of time). Then, the medicine ejection device can have a controller for switching between the state of pressurizing the movable wall and the state of not pressurizing the movable wall.

(Medicine Ejection Device)

Figure 3:
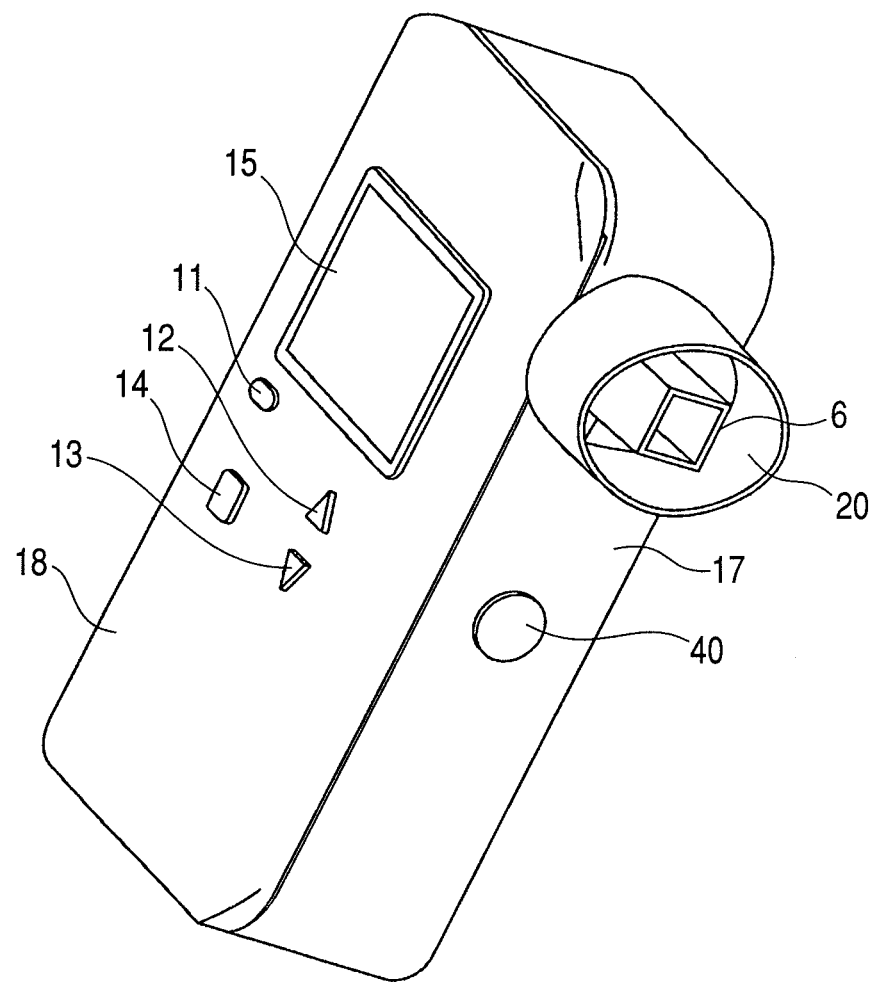
FIG. 3 is a perspective view illustrating an appearance of an inhaler for making a user inhale a medicine, which is one example of a medicine ejection device according to the present invention.

FIG. 3 is a perspective view illustrating an appearance of an inhaler for making a user inhale a medicine, which is one example of a medicine ejection device according to the present invention. An exterior package of the main body includes a housing 17 and an access cover 18. A button 40 releases a lock of the access cover. A hook member 19 (FIG. 4) provided so that the access cover 18 does not open during use is configured so as to perch on a hook-entrapping axis which works cooperating with the lock release button 40 that is pushed by a spring. The access cover 18 is configured to be opened by an operation of pushing the release button 40, which disengages the hold of the hook and makes the unshown spring apply a force of exerting the access cover 18 in a direction of opening the access cover 18, when the access cover 18 is opened. The access cover 18 is provided with a display unit 15 for displaying a dose, the time of day, an error message and the like. The access cover 18 is also provided with a menu-switching button 11, and an up button 12, a down button 13 and a determination button 14, which are setting buttons so that the user can set the menu.

Figure 4:
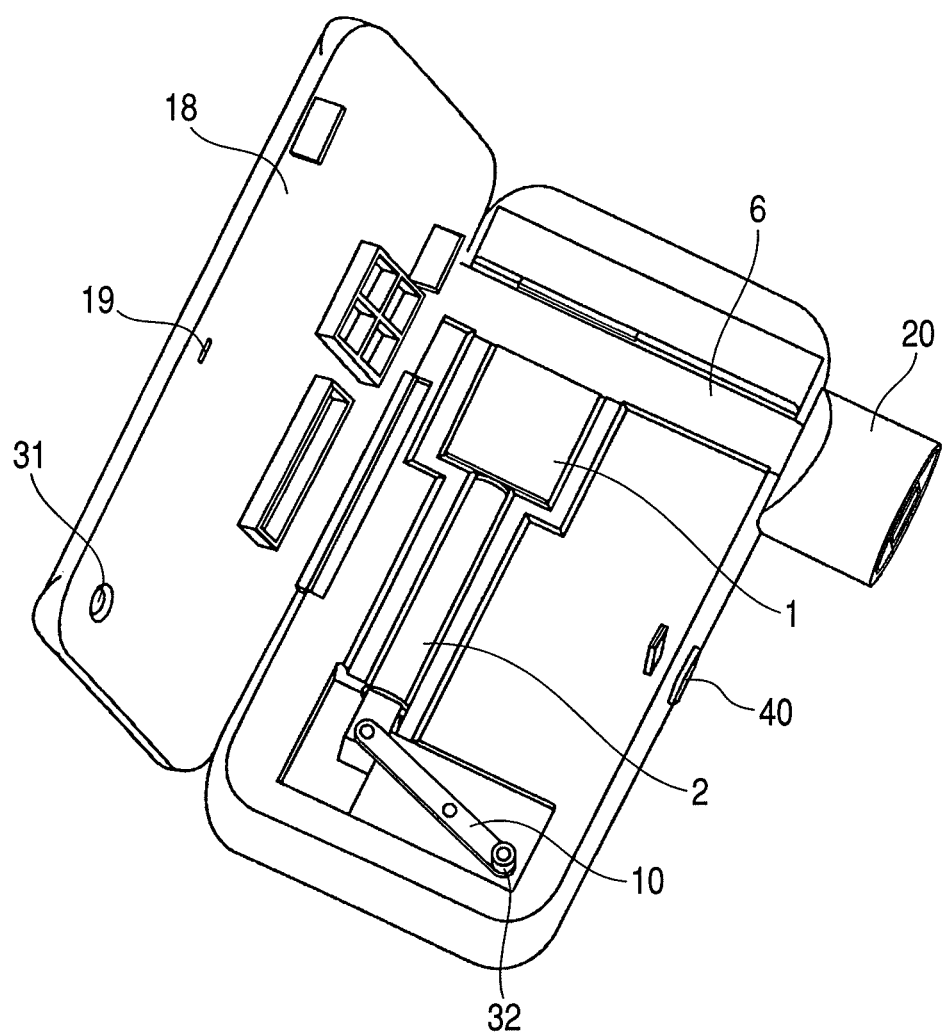
FIG. 4 is a view illustrating a state in which an access cover 18 is opened in the inhaler in FIG. 3.

FIG. 4 illustrates the state of the inhaler in FIG. 3, in which the access cover 18 is opened. When the access cover 18 is opened, an ejection head unit 1 and a reservoir 2 can be seen, which are respectively a medicine ejection portion that can be attached and detached to and from the main body of the device, and a medicine storing portion. The ejection head unit 1 ejects a medicine towards an air flow path 6. A user can inhale a medicine ejected into the air flow path by inhaling a breath from an inhalation port (mouthpiece) 20. In the present embodiment, the inhalation port (mouthpiece) 20 and the air flow path 6 are integrated. The inhalation port 20 is disposed every time when having been used for inhalation, or is reused after having been washed after inhalation. The ejection head unit 1 and the reservoir 2 are replaced when the quantity of the medicine in the reservoir 2 becomes less than the quantity of the medicine which should be administered through one time of inhalation. It is possible, for instance, to provide a function for counting an ejection amount in the main body, make the function for counting the ejection amount calculate a remaining amount and announce the replacement time and urging a user to replace the ejection unit and the reservoir, or alternatively to make the device stop ejecting the medicine until the replacement is completed.

After the ejection head unit 1 and the reservoir 2 have been fitted, they are connected and jointed by moving the reservoir 2 to the ejection head unit 1 side with a connection lever 10. Then, a flow path of the medicine is formed, through which the medicine in the reservoir flows into the ejection head unit 1. The access cover 18 has a lock hole 31 for the connection lever provided therein. Accordingly, when the access cover 18 is closed, a knob 32 of the connection lever 10 is engaged in the lock hole 31 of the connection lever. Then, the connection between the ejection head unit 1 and the reservoir 7 cannot be released, as long as the access cover 18 is not opened. The lock hole 31 prevents the reservoir 2 from being disengaged from the ejection head unit 1 when a user puts the device in a bag or the like and carries it after the reservoir 2 has been connected with the ejection head unit 1.

(Ejection Head Unit and Reservoir)

Figure 6:
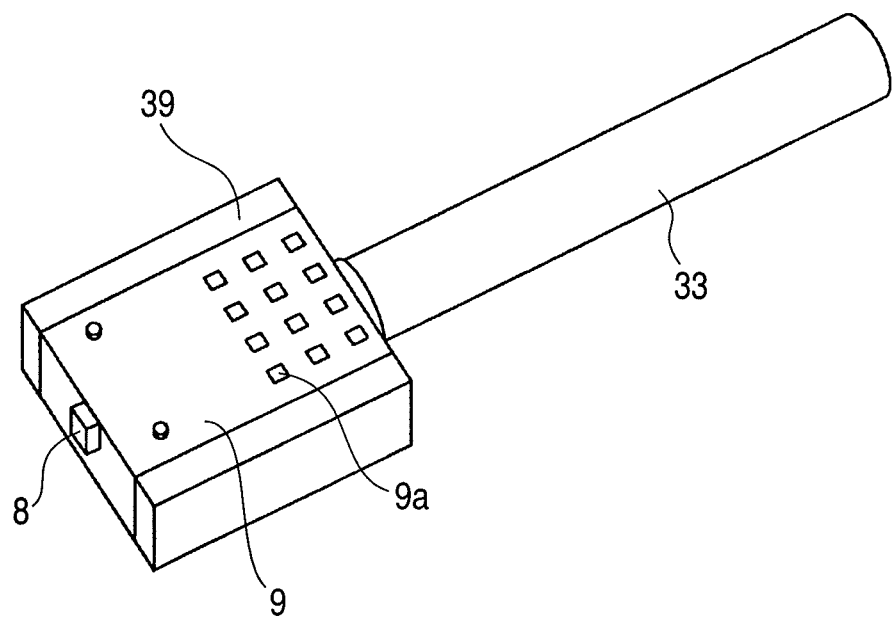
FIG. 6 is a perspective view illustrating only an ejection head unit 1 and a reservoir 2 extracted from an inhaler in a state in which the ejection head unit 1 is connected with the reservoir 2.
Figure 7:
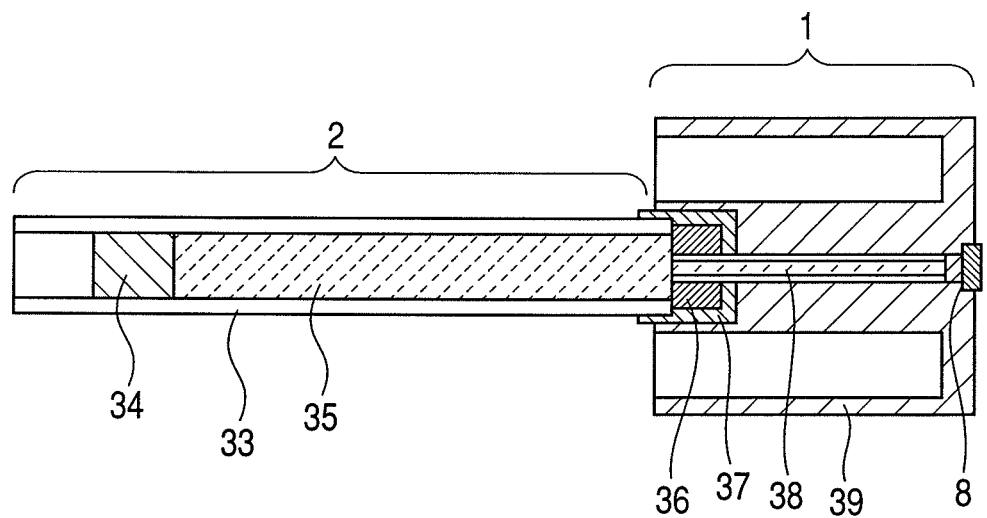
FIG. 7 is a principal sectional view illustrating the ejection head unit 1 and the reservoir 2 of a connected state in FIG. 6.

One example of a specific structure of an ejection head unit 1 and a reservoir 2, which are used in the medicine ejection device according to the present invention, will be described with reference to FIG. 5 to FIG. 7.

Figure 5:
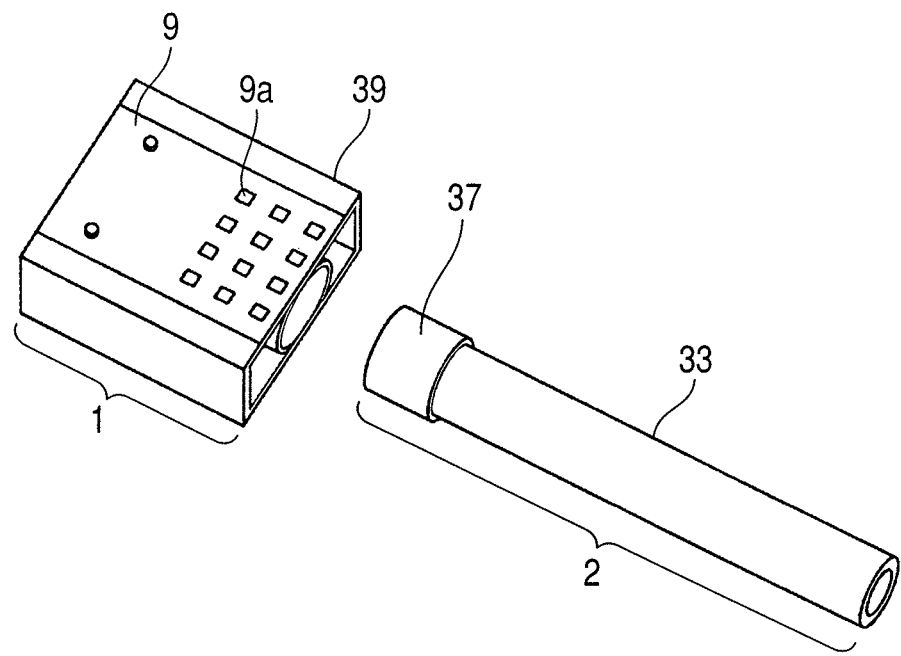
FIG. 5 is a perspective view illustrating a state of an ejection head unit 1 and a reservoir 2 which are to be connected.

FIG. 5 is a perspective view illustrating a state of an ejection head unit 1 and a reservoir 2 which are to be connected. FIG. 6 is a perspective view illustrating only a part of an ejection head unit 1 and a reservoir 2 extracted from an inhaler in a state in which the ejection head unit 1 and the reservoir 2 are connected with each other. FIG. 7 is a principal sectional view of the ejection head unit 1 and the reservoir 2 in a connected state in FIG. 6.

The ejection head unit 1 includes the components which will now be described below. Specifically, an ejection head 8 provided with a plurality of ejection nozzles is attached to and supported by a housing 39, and a hollow needle (flow path of medicine liquid) 38 is arranged in the inner part of the housing, through which the medicine is supplied from a reservoir to the ejection head 8. The ejection head 8 has a heater which is an element of generating ejection energy provided in the vicinity of the ejection nozzles, and ejects the medicine through the ejection nozzles by using the energy generated when the heated medicine foams. The ejection head unit 1 also has an electrically jointing face 9a for supplying an electric power to the heater therethrough and an electrical wiring component 9 which supports the electrically jointing face 9a. An electric power is supplied from a rechargeable battery (not shown) of a secondary battery held in the main body of the inhaler through the electrically jointing face 9a.

The reservoir 2 includes the components which will now be described below. Specifically, there is a glass container 33 for storing the medicine therein, and one end of the glass container 33 is blocked by a fixing rubber plug 36 which is fixed by a caulking fitting 37 made from aluminum. The other end of the glass container 33 has a movable rubber plug 34 inserted into the inner part of the container, which blocks the medicine from the outside air. When the ejection head unit 1 is connected with the reservoir 2, the inside of the glass container is blocked from the outside air except a path through the ejection nozzle of the ejection head 8. The reservoir keeps its sealability due to the structure, and suppresses the denaturation of the medicine and the change of the concentration to the minimum.

The ejection head unit 1 and the reservoir 2 may be structured from thus different members, but may be structured into a single piece from one member. In this case, the ejection head unit 1 and the reservoir 2 can be easily attached and detached to and from the main body of the inhaler. When a reservoir is made from glass, such a housing as to cover the reservoir is useful for preventing the reservoir from being broken when the reservoir is hit.

(Embodiment 1)

Figure 8:
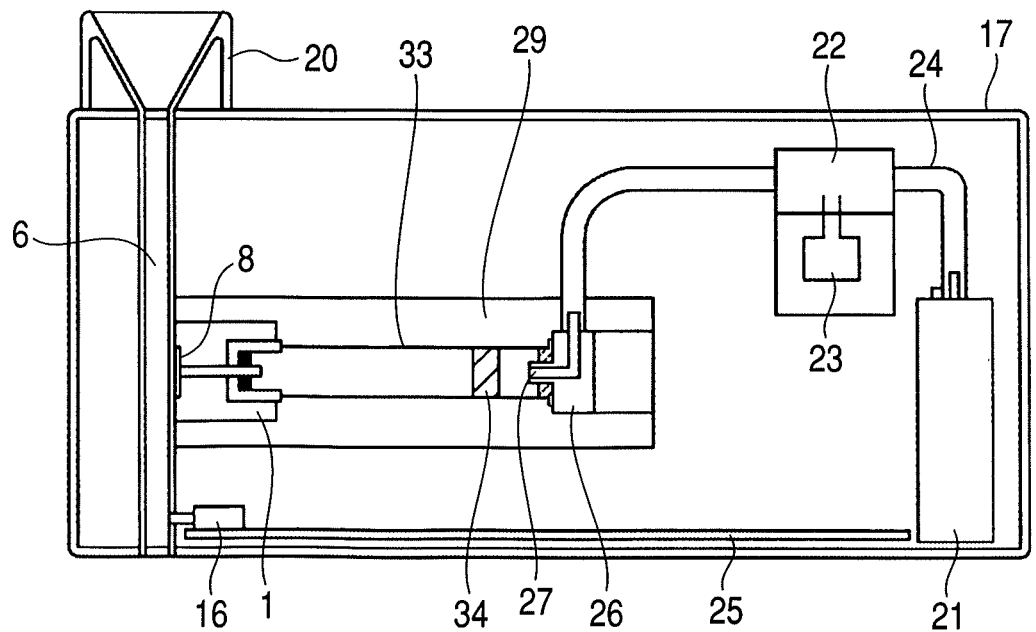
FIG. 8 is a schematic sectional view of a medicine ejection device relating to a first embodiment of the present invention.

FIG. 8 illustrates a schematic sectional view of a medicine ejection device relating to a first embodiment of the present invention. In the present embodiment, an air compressor 21 which generates a compressed air was used for a pressure unit.

Compressors are largely classified into a turbo type and a volumetric type. The turbo type is mainly used when the pressure may be low and a large quantity of air is required. On the other hand, the volumetric type is used when a high pressure is required. The compressor used in the present embodiment was an air pump which is one of the volumetric types and adopts a diaphragm drive system of generating a compressed air by moving a diaphragm up and down with a torque of a motor. An air pump of the diaphragm drive system is comparatively small, and accordingly is suitable for an inhaler which is always carried.

The compressor 21 is connected with a rubber plug 34 of a movable wall and generates a pressure to be applied to the rubber plug 34. In other words, the compressed air generated in the compressor 21 passes through an air tube 24, passes through an air supply pipe 27 held by a pressurized air joint 26, and pressurizes the movable rubber plug 34. A regulator 22 exists between the rubber plug 34 and the air compressor 21, and works as a valve mechanism for adjusting a flow rate of the air supplied to the rubber plug 34. Furthermore, the regulator 22 contains a pressure sensor 23 therein, and accordingly can measure a pressure to be applied to the movable rubber plug 34.

The medicine ejection device can adjust a pressure to be applied to the movable rubber plug by controlling the valve mechanism in the regulator 22 based on a pressure value of the pressure sensor 23. A pressure to be applied to the movable rubber plug 34 is previously set in a CPU installed in a control substrate 25, and a controller makes the regulator work so that the measured value by the pressure sensor 23 matches the set value. Specifically, the controller makes the regulator to pressurize the plug by opening a valve when the measured value by the pressure sensor 23 falls below the set value, and not to pressurize the plug any more by closing the valve when the measured value exceeds the set value. The medicine ejection device having the mechanism can pressurize the movable rubber plug 34 with a constant pressure value even after the medicine has been ejected and the movable rubber plug 34 has started moving. A pressure to be applied to the rubber plug 34 may be set at a fixed range of values. The controller may control the valve when the measured value has deviated from the range. The regulator 22 contains a D/A (Digital-to-Analog) converting part therein. The regulator 22 can be a low pressure electropnematic regulator which can regulate the pressure into a positive pressure range of about 0 to 50 kPa.

Because of thus having the regulator 22, the medicine ejection device can stabilize the pressure to be applied to the movable rubber plug 34 even when a pressure value of the compressed air generated in the compressor 21 has pulsation irregularity, so that the compressor can be selected more freely.

An example of a process for using an inhaler according to the present embodiment will be described along with the flow chart illustrated in FIG. 9.

At first, the inhaler is set at a state of being capable of starting to be used by an operation of turning an electric power switch of the main body of the inhaler on or the like by a user (S001). After the starting state, the inhaler examines whether an ejection head unit 1 is inserted therein or not (S002).

When the ejection head unit 1 is not inserted therein, the inhaler displays an alarm for informing the user the absence of the ejection head unit 1 (S015), turns the power source off (S023), and finishes its action (S024).

When the ejection head unit 1 employs, for instance, a thermal jet type for ejecting a medicine, the presence or absence of the ejection head unit 1 can be detected by measuring an ohmic value of a heater which is an ejection energy generating element.

When there exists the ejection head unit 1, the medicine remaining quantity of a reservoir 2 is checked (S003). The medicine remaining quantity is obtained by subtracting the total amount of an ejected medicine from an initial volume in the reservoir. The inhaler makes the RAM or the ROM which are provided on a control substrate store the medicine remaining quantity, and when the remaining amount is less than the amount necessary for one time of inhalation, displays an alarm (S016), turns the power source off (S023), and finishes its action (S024).

When a sufficient amount remains the reservoir, the inhaler checks a remaining amount of a battery (not shown) (S004). When the remaining amount is insufficient, the inhaler displays a message for urging the replacement or charging of the battery (S017), turns the power source off (S023), and finishes its action (S024). When the inhaler has determined that the battery remaining quantity is sufficient at least for one time of an inhaling action, the user turns the power source on (S005), and sets initial conditions (S006).

After the initialization has been completed, a medicine dose is input in the step S007. Sometimes, the user may be required to input a dose by oneself. Normally, the dose in a prescription data by a doctor is automatically set in the inhaler, but the user may change the dose, for instance, of insulin in consideration of a calorie intake and calorie consumption when the user inhales the medicine.

Subsequently, the steps will be described in which the inhaler starts pressurizing a movable wall. After a dose of the medicine has been determined, a compressor 21 generates compressed air for pressurizing an enclosed space behind a movable rubber plug 34 (S008). Here, the maximum static frictional force and a kinetic frictional force working between a glass container 33 and the movable rubber plug 34 are uniquely determined by a quality of a material of the glass container and its dimension, and a quality of a material of the movable rubber plug and its dimension. Accordingly, the user can previously set a pressurization value so that the reservoir inner pressure in an equilibrium state can be a desired value, while the rubber plug is moving after ejection. The set value is stored in a CPU in the inside of a control substrate 25. The inhaler controls a regulator 22 and a pressure sensor 23 so that the set pressure can be applied to the rubber plug (S009, S010 and S011), and waits for the start of inhalation (S012).

When the user starts inhalation, a negative pressure is generated in an air flow path 6, so that the inhaler can sense the start of inhalation through a pressure sensor 16 which is arranged on the control substrate 25. When having sensed the predetermined negative pressure (S013), the inhaler conducts ejection (S014). In such a way, the inhaler ejects the medicine in a state of pressurizing the movable wall. Here, the inhaler may synchronize the timing of a start of pressurization illustrated in S008 with the timing of the inhalation sensed by the pressure sensor 16. Thereby, the inhaler can minimize the driving action of a pressure unit.

While the inhaler is ejecting the medicine, an operation of pressure measurement interrupts the ejection (S018), and the inhaler determines whether a pressurization value is in a predetermined pressure range (S020). When the value is lower than the predetermined range, the inhaler opens a regulator valve to send the compressed air into an air supply pipe (S021). This interruption operation (S018) is periodically and repeatedly conducted during ejection. Alternatively, the inhaler may monitor the pressure value, and when the pressure value becomes lower than the predetermined range, may open the regulator valve to send the compressed air till the pressure value reaches the predetermined range. After having ejected the medicine for a set period of time, the inhaler finishes the ejection operation (S019). When having finished the ejection operation, the inhaler stores the medicine remaining quantity in a flash ROM on the control substrate 25, turns the power source off (S023), and finishes its action (S024).

Figure 10:
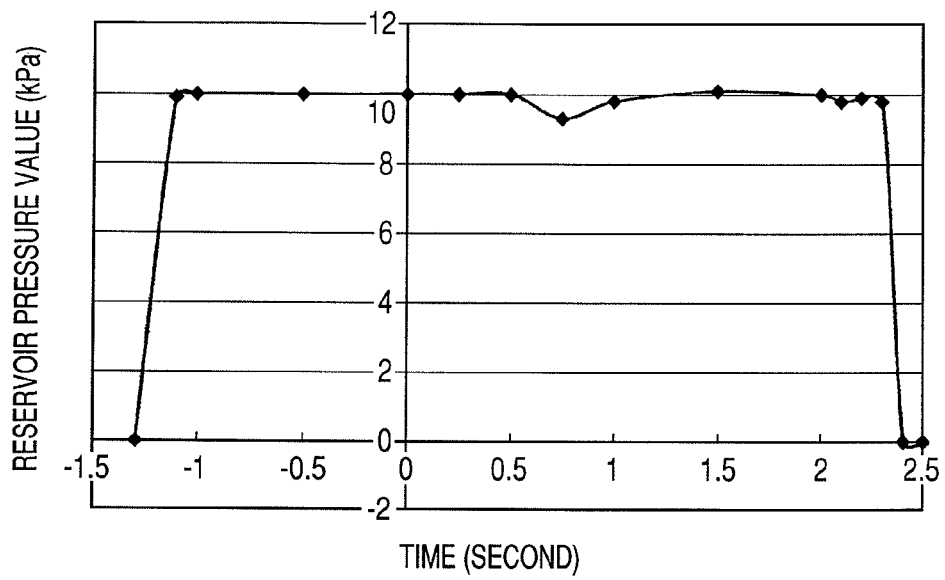
FIG. 10 illustrates one example of the change of a pressure with time, which is applied to a movable rubber plug 34 when a medicine is ejected, in Embodiment 1.
Figure 11:
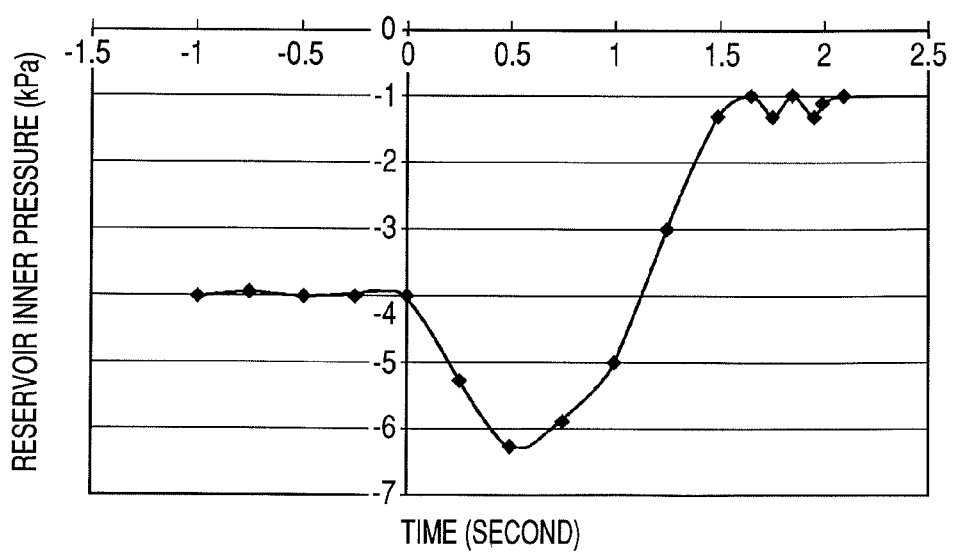
FIG. 11 is a graph illustrating a change of a pressure in a reservoir when the reservoir has been pressurized in a condition of FIG. 10.

FIG. 10 illustrates one example of the change of a pressure with time, which is applied to a movable rubber plug 34 when a medicine is ejected, in the present embodiment. FIG. 11 is a graph illustrating a change of a pressure in a reservoir when the reservoir has been pressurized in a condition of FIG. 10. The pressure in the reservoir was measured with a pressure sensor for measuring the internal pressure, which has been connected in the middle of a hollow needle (flow path of medicine liquid), which connects a glass container 33 with an ejection head 8 in FIG. 8. In both figures, the ejection is started at the timing of the zero point in a time axis (abscissa). The figures are obtained as a result of an experiment that has been carried out by making an inhaler eject pure water at a rate of 15 μl/sec for 2 seconds, which has such a structure that a reservoir is a glass container having 2 ml of the volumetric capacity and the internal diameter of Φ6.8, and has a movable rubber plug inserted therein which has the diameter of Φ7.2, the length of 6 mm and the Shore A hardness of 50 degrees.

When the glass container and the rubber plug as described above were employed, the maximum static frictional load was about 60 g, and the kinetic frictional load was about 40 g. These values correspond to about 16 kPa and about 11 kPa respectively, when converted to a pressure applied to the rubber plug (sum of pressures due to pressure difference between inside and outside of container and pressure due to pressure unit). For this reason, a pressure of 10 kPa is applied to the movable rubber plug in a whole period of ejection from the time immediately before the start of ejection. The internal pressure of the reservoir is stable at about −4 kPa before the ejection is started, but after the ejection has been started, the internal pressure changes towards a direction of a negative pressure. The pressure of 10 kPa is applied to the rubber plug beforehand, so that just approximately when a negative pressure in the reservoir has exceeded −6 kPa, the maximum static frictional load is applied to the rubber plug. Thereby, the rubber plug starts moving, and the negative pressure in the reservoir increases along with the movement. The pressure is stable in the vicinity of −1 kPa during the following ejection period.

It is also possible to apply a pressure before the time when the rubber plug starts moving higher than the pressure after the time when the rubber plug has started moving. By doing this, the inhaler can further inhibit a negative pressure in the reservoir from decreasing, because the rubber plug starts moving in an earlier moment. In this case, when a pressure to be applied to the rubber plug before the rubber plug starts moving exceeds a pressure corresponding to the kinetic frictional load, the pressure can be controlled to a pressure corresponding to the kinetic frictional load or lower by weakening the pressurization force due to the pressure unit in a moment when the rubber plug has started moving. If such an action would be taken, the inhaler can move the time when the rubber plug starts moving ahead and simultaneously can eliminate the case where the pressure unit pressurizes the rubber plug too much after the rubber plug has started moving and makes the medicine leak out from an ejection nozzle. By the way, the pressure to be added to the rubber plug before the rubber plug starts moving can be a pressure corresponding to the maximum static frictional load or lower. In such a case, it is necessary to catch the moment when the rubber plug 34 has started moving. The start of the movement of the rubber plug 34 can be easily detected because when the rubber plug starts moving, the pressure value which is output from a pressure sensor 23 that is measuring a value of a pressurization value suddenly decreases.

(Embodiment 2)

Figure 12:
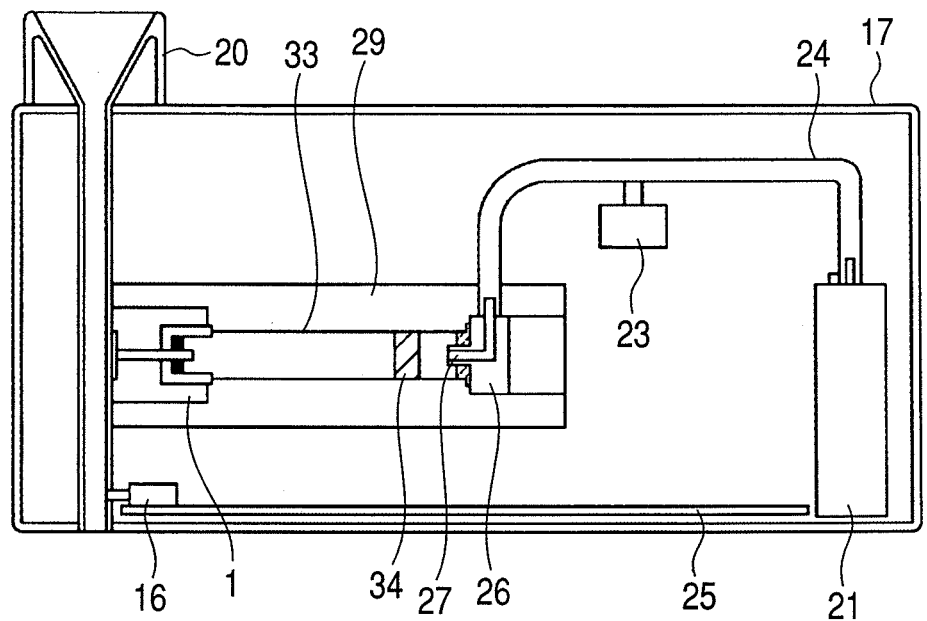
FIG. 12 is a schematic sectional view of a medicine ejection device according to a second embodiment of the present invention.

FIG. 12 is a schematic sectional view of a medicine ejection device according to a second embodiment after a regulator 22 has been removed from Embodiment 1.

In the case of this embodiment, a pressure in an enclosed space behind a movable rubber plug 34, specifically a pressure in a tube 24 can be controlled in the same way as in Embodiment 1, by making the rotation speed of an air pump 21 variable based on a measured value by a pressure sensor 23. The pressure can be regulated by increasing the rotation speed of the air pump 21 so that the measured value by the pressure sensor matches a set value when the pressure is increased, and by decreasing the rotation speed when the pressure is decreased. The volume provided on a control substrate 25 can be automatically regulated with a control signal sent from a CPU. A flow of an example of using an inhaler is similar to that in Embodiment 1 except that the switching operation for a control valve of a regulator was replaced by a controlling operation for the rotation speed of the air pump, so that the description will be omitted. When it is planned to shrink the size of and reduces the weight of the inhaler compared to that in Embodiment 1, the embodiment is effective.

(Embodiment 3)

Figure 13:
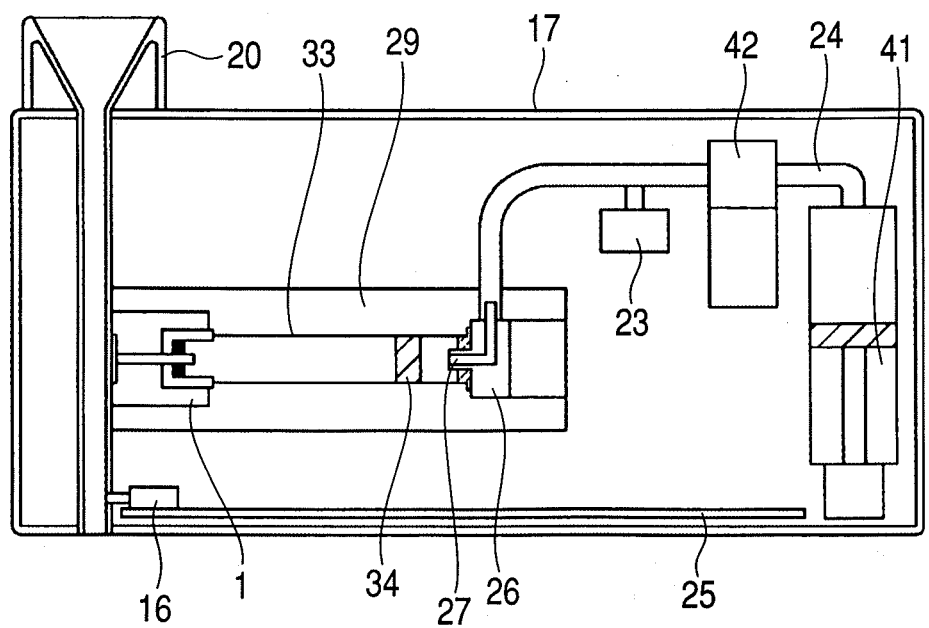
FIG. 13 is a schematic sectional view of a medicine ejection device according to a third embodiment of the present invention.

FIG. 13 is a schematic sectional view of a medicine ejection device according to a third embodiment which employs an electric cylinder 41 for a pressure unit in place of an air pump. The electric cylinder 41 is a device which changes the volumetric capacity in a cylinder contained in the inner part, by rotating a ball screw or the like by the rotation of a built-in motor, and moving a direct-acting member connected to the ball screw. The medicine ejection device can easily detect the position because of containing an encoder and the like.

The compressed air generated by a volumetric change of the electric cylinder 41 is sent to a space behind a movable rubber plug 34 in a glass container 33. An internal pressure of an enclosed space which pressurizes the movable rubber plug 34 can be easily regulated, by controlling the switching of a solenoid valve 42 based on a pressure value of a pressure sensor 23. The user returns the position of the electric cylinder 41 to the start position when mounting a reservoir in the medicine ejection device, and pushes the electric cylinder 41 to generate the compressed air in the electric cylinder 41. The medicine ejection device opens a solenoid valve 42 so that the compressed air can pressurize the plug with a fixed force along with ejection, and sends the compressed air into a space behind the movable rubber plug 34. It is possible to make the electric cylinder 41 send the air to the space so as to synchronize with the opening action of the solenoid valve 42.

In the present embodiment, the similar purpose can be achieved by making the electric cylinder 41 directly push and pull the air based on the measured value by the pressure sensor 23, even though the structure does not have the solenoid valve 42. The structure is advantageous in being capable of reducing the size and weight.

(Embodiment 4)

Figure 14:
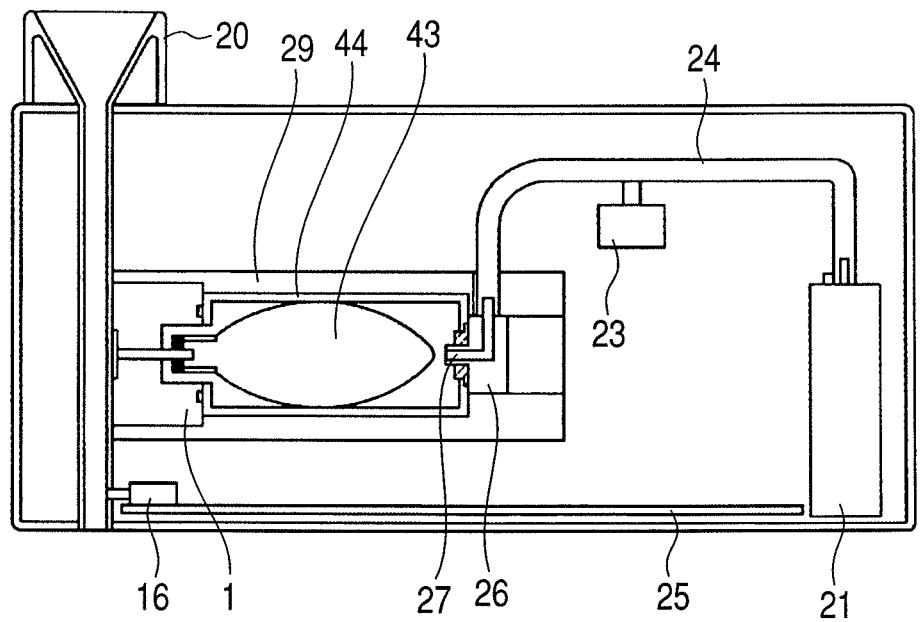
FIG. 14 is a schematic sectional view of a medicine ejection device according to a fourth embodiment of the present invention.

FIG. 14 is a schematic sectional view of a medicine ejection device according to a fourth embodiment which employs a flexible container 43 integrated with a movable wall for a reservoir.

Even when the flexible container is used, the container needs to have gas barrier properties for preventing the concentration of a medicine from changing due to evaporation and a chemical resistance for preventing the quality of the medicine from changing, similarly to the case of using a glass container and a rubber plug. For this reason, a container 43 that satisfies such conditions can employ a resin film laminated with an aluminum film or a polyethylene film having aluminum vapor-deposited thereon. The medicine ejection device adopts a method of communicating the container with an ejection head unit 1 through a hollow needle while inserting a rubber plug in the joint part. A closed space of enclosing the container 43 is formed by arranging a closed box 44 so as to surround the container 43. The medicine ejection device has a structure in which a pressure unit can pressurize the container 43 through the space. The pressure unit supplies the compressed air generated in an air pump 21 to the closed box 44 from an air feed pipe 27 through a tube 24.

The container 43 results in possessing multiple layers and a thick wall in order to secure sealability as describe above, and accordingly does not reduce the volumetric capacity (in other words, cannot be crushed) by a negative pressure of the inner part, immediately after having started the ejection of the medicine. When the negative pressure in the container 43 increases into a considerable amount before starting its deformation, the increased negative pressure causes similarly a problem of lowering an ejection performance. Then, the medicine ejection device makes the pressure unit pressurize the container from the outside so that the container can be easily deformed. Thereby, the container starts deformation in a stage at which a smaller negative pressure has been generated in the container, and accordingly the ejection performance can be maintained.

In FIG. 14, the pressure unit employs an air compressor similarly to that in Embodiment 1, but may employ another device as long as the device achieves the similar purpose.

When a glass container is employed as a reservoir, a movable rubber plug needs to move along the internal circumference of the glass container, so that the container needs to have a straight shape. However, when the container is flexible, the shape can be arbitrarily set so as to match the shape of a component which accommodates the container. Accordingly, the whole device can be miniaturized if the shape would be determined according to an empty space in the device. Accordingly, the device acquires improved portability, and becomes convenient for a user.

(Embodiment 5)

Figure 15:
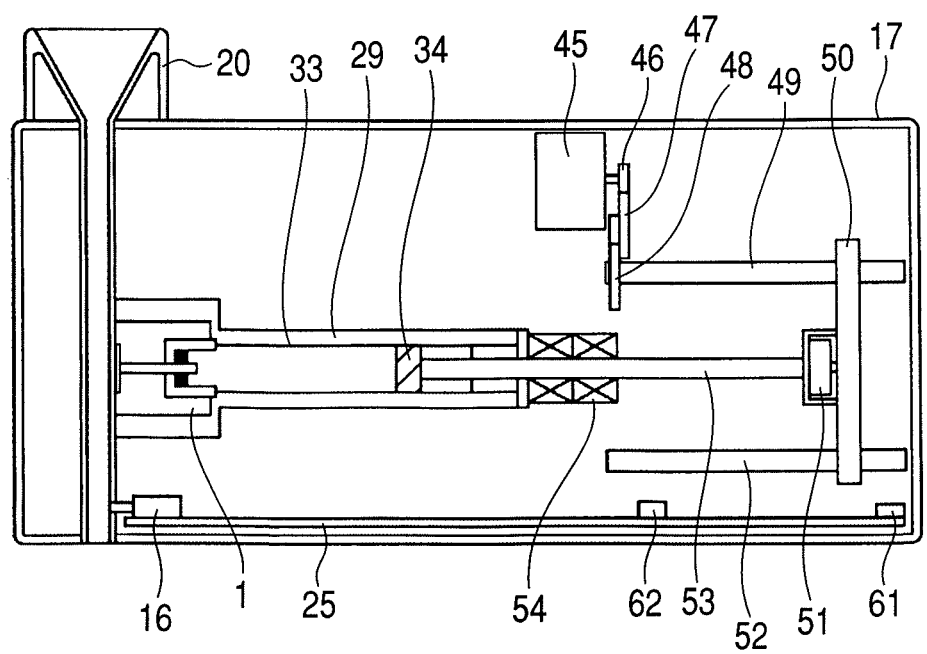
FIG. 15 is a schematic sectional view of a medicine ejection device according to a fifth embodiment of the present invention.

FIG. 15 is a schematic sectional view of a medicine ejection device according to a fifth embodiment. The present embodiment adopts a piston-pin 53 for pressurizing a movable rubber plug 34 and a motor 45 for driving the piston-pin as a pressure unit.

An ejection head unit 1 and the reservoir 2 are mounted on a cartridge holder 29 provided in a housing 17 of the main body of the device, and are connected to each other by a connection lever 10 (FIG. 4) to form a flow path in which a medicine flows to an ejection head, which is the same as in Embodiment 1.

The piston-pin 53 pressurizes the movable rubber plug 34, which is supported by a linear motion bearing (rolling bearing) 54 so as to stably move straight and is guided so as to move with a low frictional load. The piston-pin 53 is connected with a load sensor 51 which is held by a supporting plate 50. The supporting plate 50 is fixed by a guide shaft 52. A screw provided in the supporting plate 50 gears with a lead screw 49, and converts the rotation of the lead screw 49 to the translatory movement of the piston-pin 53. The drive motor 45 generates the rotation driving force of the lead screw 49. In other words, the pressure unit has a structure in which the rotation driving force of the drive motor is transmitted to a lead screw gear 48 which is fixed to the lead screw, from a motor gear 46 through a driven gear 47. When the reservoir is mounted, the piston-pin 53 needs to return to the home position, so that the drive motor 45 can be a reversible motor. Accordingly, the drive motor 45 can be a direct-current motor, or a stepping motor. A malfunction and the like can be prevented by installing a switch 61 for detecting a starting home position and a switch 62 for the position of a stroke end on a control substrate 25, and making a mechanical type of a micro-switch, or a non-contact-type of a proximity switch or an optical switch detect the position of the supporting plate 50 for the load sensor.

A pressure is the quotient obtained by dividing a load by a cross-section area, so that the load and the pressure are in proportional relation as long as the cross-section area is constant. Accordingly, a pressure value to be applied to the movable rubber plug 34 by the piston-pin can be measured as a load value of the load sensor 51, according to the structure. Therefore, the pressure unit may push the piston-pin 53 so that the pressure value (or the range) set up beforehand can be maintained.

Figures 9, 9A, 9B:
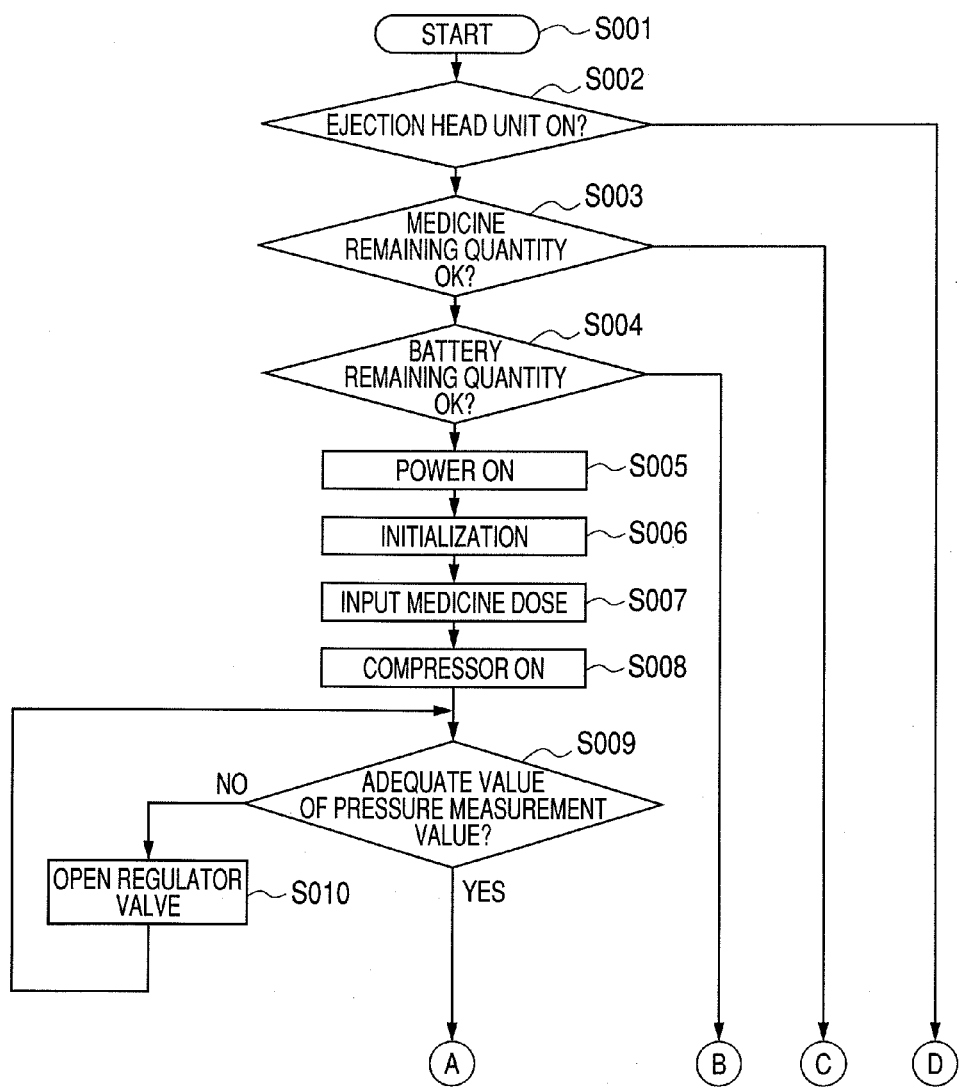
FIG. 9 which is comprised of FIGS. 9A and 9B are flow charts illustrating an example in which an inhaler according to Embodiment 1 is used.
Figure 9B:
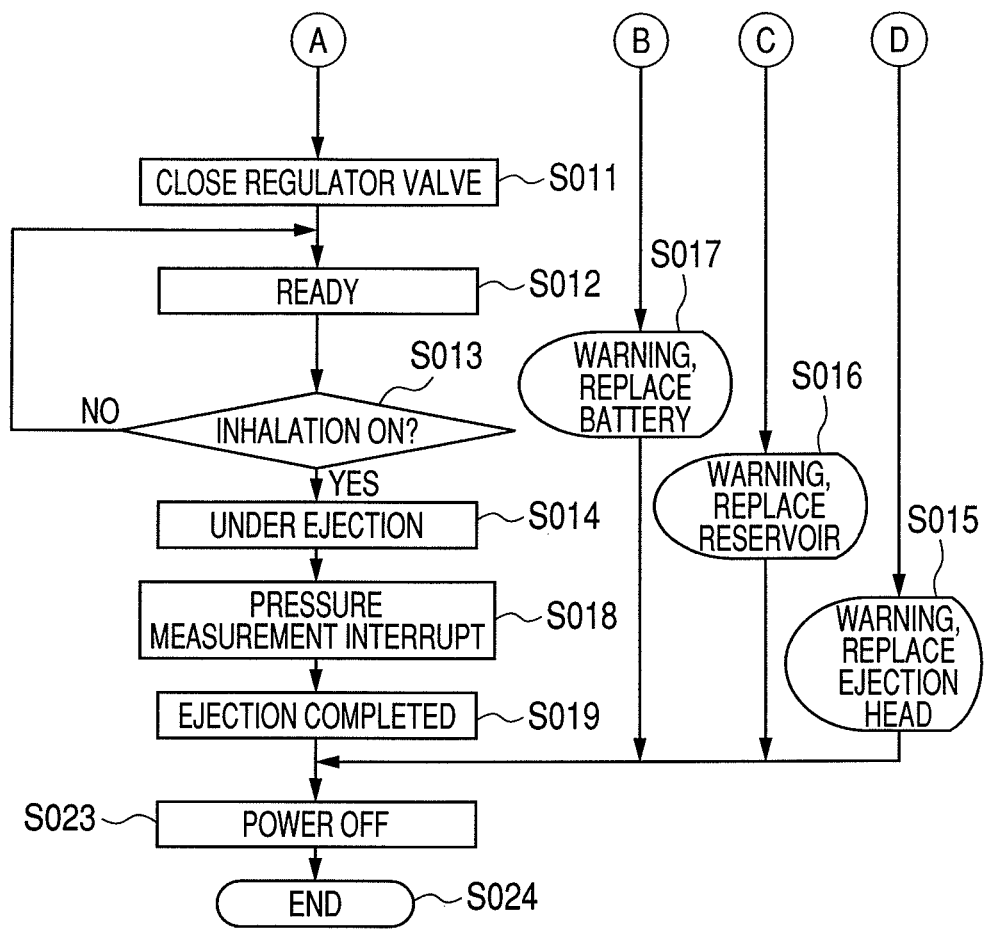
Figure 9B:
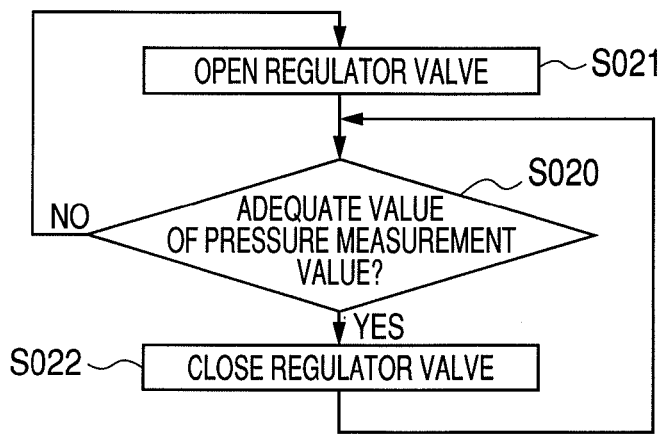

A flow of an example of using an inhaler is basically similar to that in FIG. 9. However, in an initialization step of S006, an operation of returning the piston-pin to the home position is necessary. Afterwards, the pressure unit makes the piston-pin 53 proceed forward by rotating the drive motor 45 and contact the movable rubber plug 34. When the piston-pin 53 contacts the movable rubber plug 34, a load value of the load sensor 51 begins to rise, and when the load value has reached the value set up beforehand, the drive motor 45 stops its rotation in order to stop the advance of the piston-pin 53. The set value changes depending on the frictional force working between a container and the rubber plug, and how much the reservoir inner pressure is desired to be maintained during ejecting, as was already described.

When the rubber plug 34 starts moving after ejection, the load which has been applied to the load sensor 51 decreases. Then, the pressure unit makes the piston-pin 53 proceed forward by rotating the drive motor 45 so as to approach the load to a set load value again. The pressure unit can apply a constant pressure to the rubber plug 34 during ejection by repeating the process.

(Embodiment 6)

Figure 16:
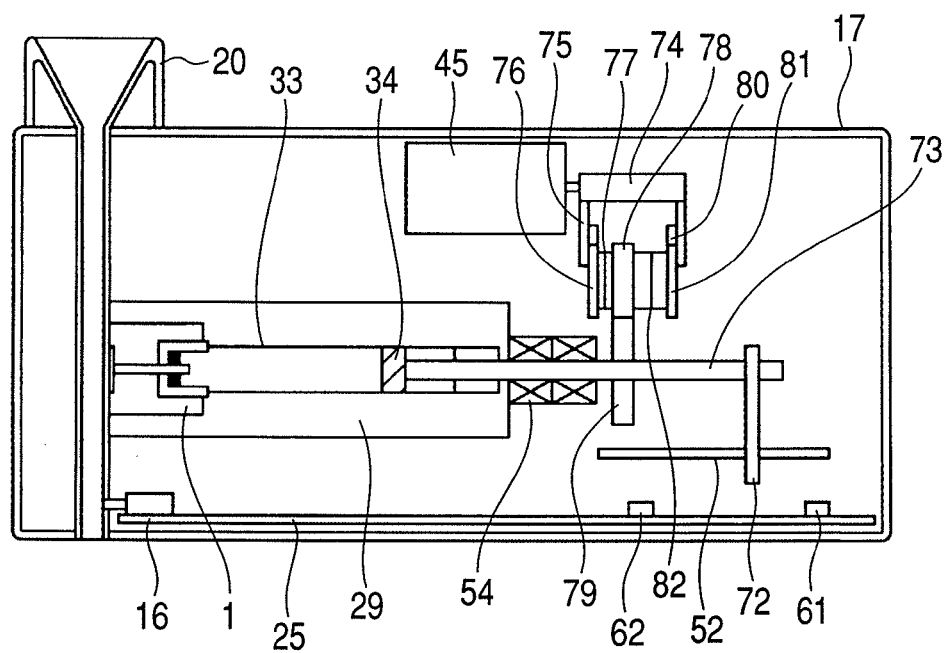
FIG. 16 is a schematic sectional view of a medicine ejection device according to a sixth embodiment of the present invention.

FIG. 16 is a schematic sectional view of a medicine ejection device according to a sixth embodiment. The present embodiment has a structure of providing a slip clutch between a piston-pin and a motor which are a pressure unit.

A piston screw 73 pressurizes a movable rubber plug 34, which is supported by a bearing 54 so as to stably move straight and is guided so as to move with a stabilized frictional load. The piston screw 73 has a screw formed around the outer circumferential part, and gears with a screw gear 79 having a gear formed in the inner circumference. The screw gear 79 gears with a transmission gear 78. The transmission gear 78 is connected with a slip clutch 77 which transmits a running torque not larger than a certain level of a friction torque to the transmission gear 78 from a transmission gear 76. A running torque is generated by a drive motor 45 and is transmitted to the transmission gear 76 through a motor gear 74 and a transmission gear 75. In other words, the piston screw 73 pushes the movable rubber plug 34 with a running torque which is generated by the rotation of a drive motor 45 and is set in the slip clutch 77. Accordingly, the piston screw 73 can always apply a constant force to the movable rubber plug 34.

When the medicine ejection device returns the piston screw 73, the medicine ejection device makes the drive motor 71 rotate in a direction contrary to the time when the piston screw 73 was pushed in. Then, the running torque is transmitted to a transmission gear 80, a transmission gear 81, and then to the screw gear 79 through the slip clutch gear 78. The transmission path is connected only when the drive motor is rotated in a reverse direction, because a oneway clutch 82 is incorporated in between the screw gear 79 and a transmission gear 81. The slip clutch gear receives only a force of the rotation in a forward direction, when the drive motor rotates in a forward direction.

A detent sheet 72 and a guide shaft 52 fixed to the piston screw 73 stop the rotation of the piston screw 73. The detent sheet 72 and the guide shaft 52 prevent the piston screw 73 from being rotated by the torque of the screw gear 79 and stopping going straight.

The drive motor 45 can be a direct-current motor having a little fluctuation of a torque, in order to continue rotating.

A flow of an example of using an inhaler is basically similar to that in FIG. 9, but in the present embodiment, it is not necessary to periodically or always sense a pressure applied to the movable rubber plug 34 with a pressure sensor or a load sensor as is in the previous embodiments. Therefore, the flow is simple. Specifically, the medicine ejection device can always apply a constant pressure to the movable rubber plug 34 by previously setting a torque corresponding to the pressure which is desired to be applied to the movable rubber plug 34, in the slip clutch 77.

The medicine ejection device rotates the drive motor 45 before starting ejection to make the piston screw 73 advance. After the piston screw 73 has started contacting the movable rubber plug 34, the piston screw 73 continues pushing the movable rubber plug 34 till the reaction force reaches a friction torque set in the slip clutch 77. When the reaction force exceeds the set friction torque, the slip clutch causes a slip. Accordingly, the pressure in the reservoir does not become an excess value.

When the internal pressure in the reservoir falls during ejection and the movable rubber plug moves, the piston screw 73 advances because the set friction torque is applied to the movable rubber plug 34. Thus, the piston screw 73 continues the action of pushing the movable rubber plug 34 by the distance corresponding to the decrease of the pressure due to the movement, during ejection.

The present embodiment has such a very simple structure as not to need a load sensor. Accordingly, the present embodiment has an advantage that the medicine ejection device hardly causes a failure, which is an important factor for medical equipment.

(Embodiment 7)

In a seventh embodiment, a medicine ejection device will be described which can make the total amount of an ejected medicine constantly equal at every use while using a structure in which a glass container and a rubber plug are employed for a medicine storing portion, among embodiments of the present invention described till now.

In the case of a device which ejects a medicine by using an electrothermal transducer as an ejection energy generating element (thermal jet type), for instance, the device causes nozzle clogging that is a phenomenon in which the medicine sticks in an ejection nozzle when having been left in the air after the medicine has been ejected once. For this reason, when the medicine is ejected in the same ejection condition (such as ejection frequency and ejecting operation duration), the total amount of the ejected medicine in one use has had a tendency of decreasing as the number of ejection times increases. It is possible to recover the state by absorbing the liquid every time before starting ejection like in an ink jet printer. However, the medicine is very expensive compared to ink, and accordingly should not be used in vain if possible.

Thus, a medicine ejection device is desired which can make the total amount of the ejected medicine constant at every time even when an ejection head of having caused nozzle clogging therein and having decreased ejection performance is used. The present embodiment provides the medicine ejection device.

Here, in the present specification, "ejecting operation duration" means a period between the time when the ejection energy generating element has received a first pulse and the time when the ejection energy generating element receives the last pulse in one use, in other words, a period while a pulse train for generating ejection energy is supplied. "Ejection frequency" corresponds to the number of the pulse signals which are given to the ejection energy generating element per unit time so as to eject the medicine. In addition, "pulse width" is a current-carrying period of time in applied one pulse signal. "Driving voltage" is a voltage to be given to an ejection energy generating element. When these driving conditions for the ejection head do not change, ejection energy to be given to the medicine does not change, but when a nozzle is clogged up, the amount of the medicine to be really ejected tends to decrease.

Figure 17:
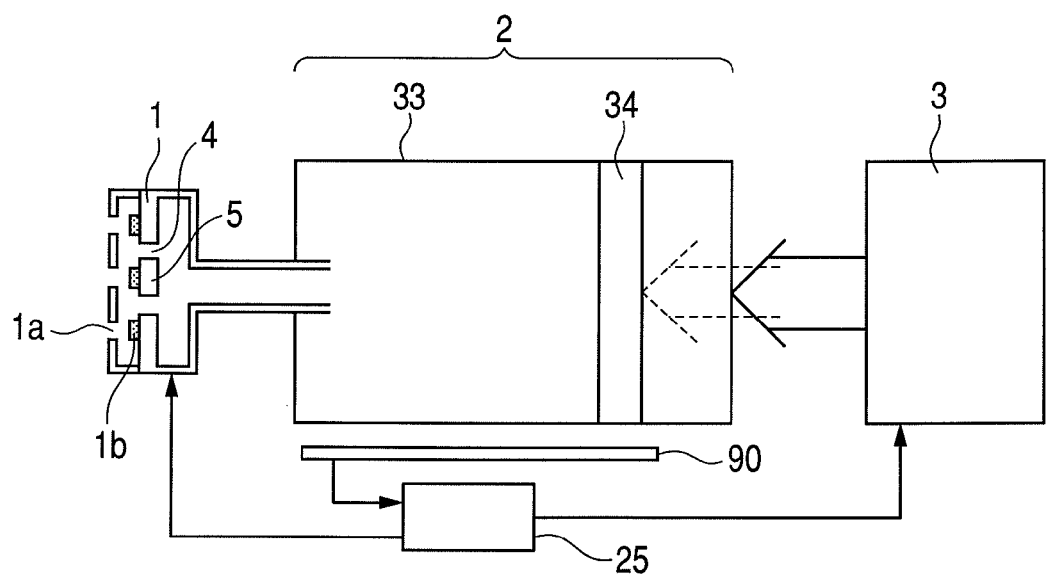
FIG. 17 is a schematic sectional view of a medicine ejection device according to a seventh embodiment of the present invention.

FIG. 17 is a schematic view conceptually illustrating a structure of a medicine ejection device according to the present embodiment. A medicine storing portion 2 is arranged in a glass container 33 and one end thereof, and includes a movable rubber plug 34 which blocks a medicine from the outside air. A pressure unit 3 applies a predetermined pressure to the movable rubber plug 34. Here, the medicine ejection device according to the present embodiment has a reading unit 90 which can detect the position of the movable rubber plug 34 and read the moving amount.

The total amount of an ejected medicine in a period after the medicine ejection device has started ejection and before the rubber plug 34 starts moving depends on a negative pressure in a reservoir of an early stage and the maximum static frictional load, and accordingly is previously known. In addition, after the rubber plug 34 has started moving and a pressure to be applied to the rubber plug 34 by the pressure unit has reached an equilibrium state with a kinetic friction load, the moving amount of the rubber plug 34 is in a linear relation with an amount of the ejected medicine, specifically, an amount of a reduced medicine in the reservoir, as long as the pressure to be applied to the rubber plug 34 is constant. Accordingly, the moving amount of the rubber plug 34 corresponds to the amount of the ejected medicine in a one-to-one relationship.

Then, the total amount of the ejected medicine in a period between the time when the ejection has been started and the time when the moving amount of the rubber plug 34 is read can be determined, by reading the moving amount with the reading unit 90. The amount of the medicine which should be administered is set in the medicine ejection device beforehand based on a prescription or the like. Accordingly, when a read result obtained from the reading unit 90 has reached the amount of the medicine which should be administered, the medicine ejection device stops the driving of an ejection energy generating element 1b through a controller 25. Thereby, the medicine ejection device can eject a constant amount of the medicine every time regardless of the ejection performance of an ejection head, even when clogging has occurred in the nozzle, and can solve a problem that an inhaled amount changes every time the medicine ejection device is used. In addition, the medicine ejection device can make the ejection amount constant even when the internal pressure of a medicine container becomes lower than −5 kPa and enters a region in which the ejection amount decreases.

Figure 18:
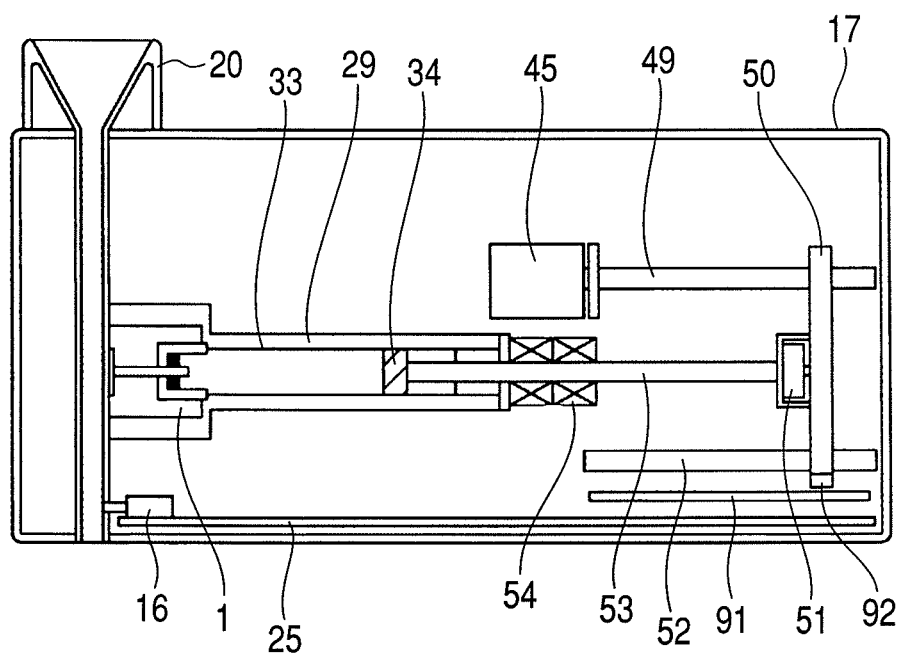
FIG. 18 is a schematic sectional view of a medicine ejection device according to Embodiment 7 of the present invention.
Figure 19:
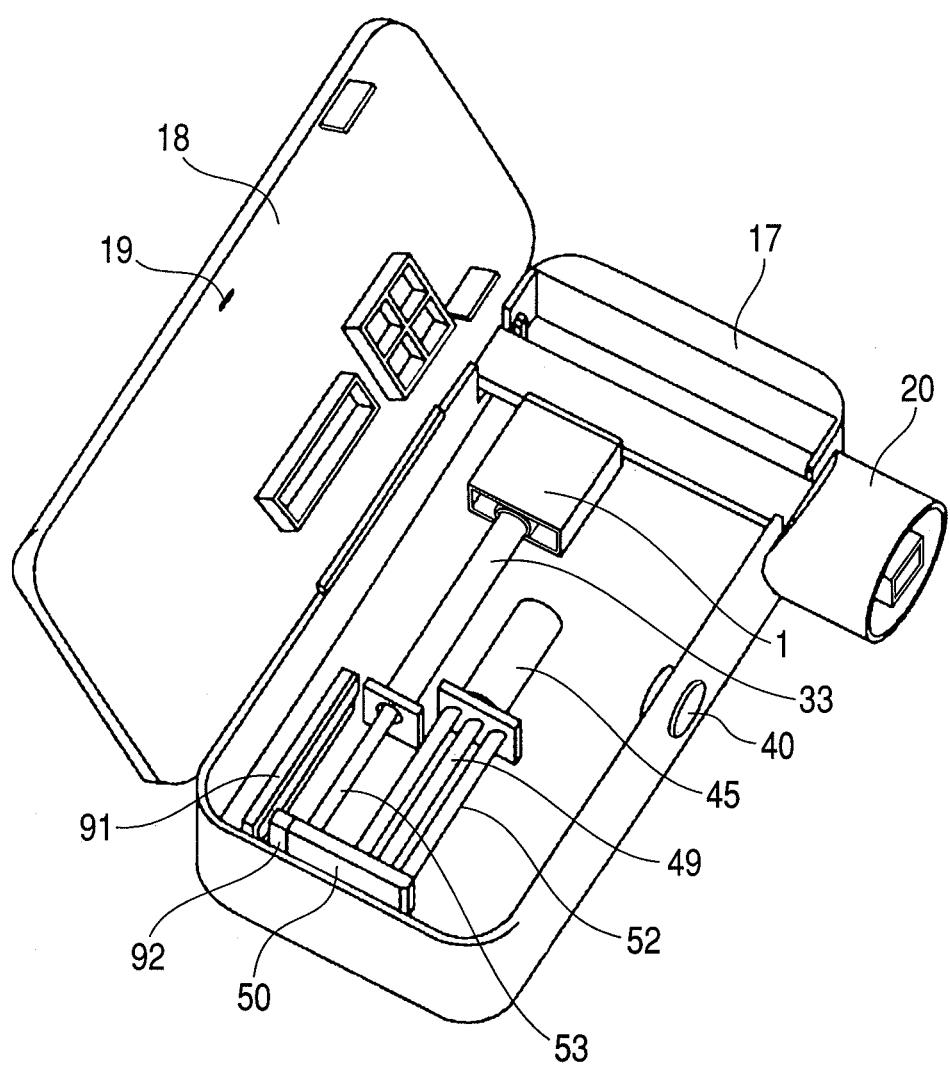
FIG. 19 is a perspective view of a medicine ejection device in a state of having removed a protective cover of the inside of the device so that a reading unit according to Embodiment 7 can be viewed.

FIG. 18 is a schematic sectional view of a medicine ejection device according to the present embodiment. FIGS. 19A and 19B are perspective views of a medicine ejection device in a state of having removed a protective cover of the inside of the device so that a reading unit according to the present embodiment can be viewed.

The device has the same basic structure as in Embodiment 5 (FIG. 15), and has adopted a piston-pin 53 for pressurizing a movable rubber plug 34 and a motor 45 for driving the piston-pin, for a pressure unit.

The piston-pin 53 pressurizes the movable rubber plug 34, which is supported by a linear motion bearing (rolling bearing) 54 so as to stably move straight and is guided so as to move with a low frictional load. The piston-pin 53 is connected with a load sensor 51 which is held by a supporting plate 50. The supporting plate 50 is fixed by a guide shaft 52. A screw provided in the supporting plate 50 gears with a lead screw 49, and converts the rotation of the lead screw 49 to the translatory movement of the piston-pin 53. The drive motor 45 generates the rotation driving force of the lead screw 49. As was already describe, the piston-pin 53 can pressurize the movable rubber plug 34 with an arbitrary pressure due to an action of the load sensor 51, and can also pressurize the plug 34 with a constant pressure during the ejection period.

Even when the medicine ejection device has a structure of having no load sensor, the piston-pin 53 can regulate the pressurizing force. The method is to use a direct-current motor as a drive motor. Then, the direct-current motor can vary a pressurization value which is applied to a rubber plug, by using generally known characteristics that a generated torque and a driving current of the drive motor are in a proportional relationship. A driving current which is generated by a pressure that is applied to the rubber plug is determined, by subtracting a driving current in a constant no-load state in which a load of a pressure is not applied to the rubber plug from a driving current of the motor. In other words, a pressurizing force applied to the rubber plug can be varied by varying a driving current in a constant-current driving method.

A reading unit 90 includes a linear scale 91 on which tick marks are labeled, and a photo sensor 92 which is fixed on the supporting plate 50. The photo sensor 92 moves in a thrusting direction together with the supporting plate 50, when the rubber plug 34 moves and the piston-pin 53 moves. The photo sensor 92 can be a transmission type of a photo-interrupter or a reflection type of a photo-reflector. In any type, a light emitting diode working as a light emitting element and a photo-transistor working as a light receiving element are incorporated in one case. In the case of the transmission type, the light emitting element is arranged so as to face the light receiving element, and the linear scale 91 of a transparent body on which tick marks are printed may be arranged between the light emitting element and the light receiving element. In the case of the reflection type, the light emitting element and the light receiving element direct to the same point on a linear scale plane while having a certain degree of an angle when viewed from the same plane side, and accordingly need to be arranged so that the gap between themselves and the linear scale plane can have such a distance that the optical axis of the light emitting element matches that of the light receiving element. The reflection type is also easily affected by a disturbance light, and accordingly is arranged at a space suitable for the photo sensor.

Light emitting and receiving faces of the photo sensor 92 can read the moving amount of the piston-pin 53 by reading the tick marks printed on the linear scale 91. The piston-pin 53 is connected with the movable rubber plug 34, so that the moving amount of the piston-pin 53 is directly a moving amount of the rubber plug 34. Here, when the technical thought for the present embodiment is considered, a method of detecting a moving amount of something, which corresponds to the moving amount of the rubber plug in one-to-one relation, is included in the present invention, because the method indirectly detects the moving amount of the rubber plug. A similar purpose is achieved by employing a system of arranging a rotary encoder on a rotation axis, as a method of catching the moving amount from a rotation quantity of the motor 45 instead of the movement of the piston-pin 53. Of course, a method of directly measuring the moving amount of the rubber plug 34 may be employed.

A flow of an example of using an inhaler is basically similar to that in FIG. 9. However, in the present embodiment, the ejection is finished when the rubber plug 34 has moved just by a previously set distance, though the ejection is finished when a set ejection period has elapsed (S019) in FIG. 9. Accordingly, when the ejection performance has decreased, the medicine ejection device has to continue ejection, for instance, for a longer period so as to eject the same amount of the medicine every time. Then, the user is very likely to finish the inhalation before the medicine ejection device has finished the ejection of a previously set amount of the medicine to be administered, which is specified in a prescription or the like.

(Embodiment 8)

For this reason, the medicine ejection device in an eighth embodiment makes a driving condition of an ejection head change in the medicine ejection device shown in the Embodiment 7, so as to be capable of completing the ejection of a predetermined amount of the medicine earlier when the ejection performance of an ejection head 8 becomes lower than a previously set threshold value.

Indices to be used when measuring the ejection performance of the ejection head 8 include following two parameters. A first one is a period between the time when the ejection has been started and the time when a rubber plug 34 starts moving. When the materials of a glass container 33 and the rubber plug 34 are decided, the maximum static frictional force is previously known. Therefore, when the ejection has been started by an unused ejection head 8 in a certain driving condition, the period before the rubber plug starts moving after the ejection has been started is previously determined. The period of time is supposed to be T1.

However, if a real period of time T spent before the rubber plug 34 starts moving would be 2 times longer than T1, which means that the ejection performance of the ejection head is 50% of that in the unused condition, the medicine ejection device spends 2 times longer period of time when having ejected the medicine in the same driving condition. Then, when $T=x \times T1$ (where x is an arbitrary numeric value not less than 1), in other words, when T is longer than the predetermined period of time, the medicine ejection device changes the driving condition so that the ejection amount per unit hour increases.

A second parameter is a moving speed V of the rubber plug 34. The parameter can be easily measured by a linear scale 80 and a photo sensor 81. Then, suppose that the moving speed of the rubber plug 34 is V1 in the case when an unused ejection head has been used. When $V=x \times V1$ (where x is an arbitrary numeric value not less than 1), in other words, when V is smaller than a predetermined speed, the medicine ejection device changes the driving condition so that an ejection amount per unit hour increases.

The ejection amount per unit hour may be increased by the following method. At first, the ejection amount can be increased by increasing ejection frequency. Alternatively, the ejection amount may be increased by increasing a pulse width or a driving voltage. The ejection amount per unit hour can also be increased and decreased by changing a single parameter out of those driving conditions for ejection or by changing a plurality of parameters in combination. A correction method suitable for an inhalation method of a user may be selected.

The end of ejection is determined from the moving amount of the rubber plug 34 similarly to that in Embodiment 7.

A medicine ejection device according to the present invention can be used in various types of application fields other than the inhalation of a medicine. The medicine ejection device can also be used for a device for ejecting a flavoring agent or the like in a form of mist and an inhaler of luxury goods such as nicotine. In this way, the medicine ejection device according to the present invention can be applied to various applications in which a reliable and hygienic ejection is needed.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2007-298173, filed Nov. 16, 2007, which is hereby incorporated by reference herein in its entirety.

The invention claimed is:

1. A medicine ejection device for ejecting a medicine, comprising:
    a medicine ejection portion having an ejection nozzle and an element that generates energy for ejecting a medicine from the ejection nozzle;

a medicine storing portion that is connected to the medicine ejection portion and stores the medicine therein, the medicine storing portion being blocked from outside air except for a path through the ejection nozzle;

a movable wall, which is displaced by a pressure difference between an inside and an outside of the medicine storing portion caused by an ejection of the medicine through the ejection nozzle to decrease a volumetric capacity of the medicine storing portion;

a pressure unit for pressurizing the movable wall so as to decrease the pressure difference;

a reading unit for reading a displacement of the movable wall corresponding to an ejection amount of the medicine and providing a reading result; and a controller that computes, based on the reading result obtained from the reading unit, a period between a time when the ejection has started and a time when the movable wall starts moving or a moving speed of the movable wall, and changes a driving condition of the medicine ejection portion so as to increase an ejection amount per unit hour when the period between the time when the ejection has started and the time when the movable wall starts moving is longer than a predetermined period of time, or when the moving speed of the movable wall is smaller than a predetermined speed.

2. The medicine ejection device according to claim 1, comprising a controller of the pressure unit for switching between a state of pressurizing the movable wall and a state of not pressurizing the movable wall.

3. The medicine ejection device according to claim 1, comprising:
a sensor for measuring a pressure applied to the movable wall by the pressure unit, and
a controller for controlling the pressure unit according to a value measured by the sensor.

4. The medicine ejection device according to claim 1, wherein the pressure unit comprises:
an air compressor or an electric cylinder which is connected to the movable wall and generates a pressure to be applied to the movable wall, and
a valve for adjusting a flow rate of air supplied to the movable wall between the movable wall and the air compressor or the electric cylinder.

5. The medicine ejection device according to claim 1, wherein the pressure unit comprises:
a piston-pin for pressurizing the movable wall,
a motor for moving the piston-pin, and
a slip clutch installed in between the piston-pin and the motor.

6. The medicine ejection device according to claim 1, wherein the device stops drive of the medicine ejection portion when the reading result obtained from the reading unit has reached a value corresponding to an amount of the medicine to be administered.

7. A method for controlling the medicine ejection device according to claim 1, comprising the steps of:
starting pressurization of the movable wall which is displaced so that the volumetric capacity of the medicine storing portion can be decreased, by a pressure difference between the inside and the outside of the medicine storing portion, which is caused by the ejection of the medicine through the ejection nozzle; and
driving the element in a state of pressurizing the movable wall to make the element eject the medicine.

* * * * *